US00PP10535P

United States Patent [19]

Holtkamp, Sr.

[11] Patent Number: Plant 10,535

[45] Date of Patent: Aug. 4, 1998

[54] AFRICAN VIOLET PLANT NAMED MEXICO CITY

[75] Inventor: Reinhold Holtkamp, Sr., Rees-Haffen, Germany

[73] Assignee: International Plant Breeding A.G., Bern, Switzerland

[21] Appl. No.: 797,616

[22] Filed: Feb. 7, 1997

[51] Int. Cl.[6] ..... A01H 5/00

[52] U.S. Cl. ..... Plt./69.2

[58] Field of Search ..... Plt./69.2

*Primary Examiner*—James R. Feyrer
*Assistant Examiner*—Melissa L. Kimball
*Attorney, Agent, or Firm*—Foley & Lardner

[57] ABSTRACT

A new and distinct cultivar of African violet named Mexico City, as described and illustrated, and particularly characterized by its extra large growth habit (35–45 cm in diameter); large, star-shaped, dark purplish blue flowers with wavy petal tips; strong stems which curve toward the center to form a bouquet above the leaves; profuse flowering; very large, dark green, heart-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Mexico City.

The new cultivar was referred to during the breeding and selection process by the designation O 4-1/31 and is a product of a planned breeding program. The cultivar was originated from a cross made by me in the controlled breeding program in Haffen, Federal Republic of Germany. The female, or seed parent, was a cultivar designated 131. The male, or pollen parent, was a cultivar designated 800 bl.

Mexico City was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Mexico City has not been observed under all possible environmental conditions. The phenotype may vary significantly with variations in environment such as temperature, light intensity and day length. The following observations, measurements and values describe the new cultivar as grown in a 15 cm pot in Haffen, West Germany and Nashville, Tenn. under greenhouse conditions which closely approximate those generally used in commercial practice.

The following traits have been repeatedly observed and are determined to be basic characteristics of Mexico City, which in combination distinguish this african violet as a new and distinct cultivar:

1) Mexico City will grow as large as 35–45 cm in diameter.

2) Large star-shaped, dark purplish blue flowers with wavy petal tips.

3) Strong, wirelike and upright flower stems curving toward the center.

4) First flash of flowers forms a bouquet above the leaves.

5) Profuse flowering.

6) Each plant carries 10–12 and more upright flower stems each of which carries 11–13 and more flowers.

7) Long lasting, non-dropping flowers.

8) Plant saleable 10 to 11 weeks after planting of unrooted shoot.

9) Seed capsules push slightly through.

10) Very large dark green, heart-shaped leaves.

11) After maturity the flowers dry off, and remain on the peduncle without becoming infected by botrytis.

The new cultivar is most similar to Vienna, disclosed in U.S. plant Pat. No. 8,120. Similarities are the extra large growth habit and purplish blue color. However, Vienna has single and smaller blossoms as well as spear-shaped leaves whereas Mexico City has large, star-shaped blossoms and heart-shaped leaves.

The accompanying color photographic drawing shows a typical specimen plant of the new cultivar grown in a 15 cm pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Mexico City.

Parentage:

*Male parent.*—800 bl.

*Female parent.*—131.

Propagation: The new cultivar holds its distinguishing characteristics through successive propagations by leaf cuttings.

Plant: From 11 cm to 14 cm tall when grown in pots, and 35–45 cm in diameter when fully grown.

*Leaves.*—General form: Heart-shaped. Diameter: 80–90 mm wide and 90–105 mm long. Texture: Velvety. Aspect: Hairy, shiny, slightly serrated. Veins: Upperside: visible; underside: well pronounced, light green to purplish red, shiny. Color (upperside): Yellow-green group 147 A and darker. Color (underside): Greyed-purple group 186 C. Petiole: Strong, purplish brown, hairy.

*Flowers.*—Buds: Bell-shaped, 7–8 mm just before opening, light green with purplish blue touch. Sepals: Five (5). Color: Purplish brown. Calyx: Shape: Funnel-shaped. Aspect: Spear-shaped, hairy. Peduncle: Character: Strong upright, hairy. Color: Purplish brown. Individual flowers: Size: 50–55 mm. Shape: Star-shaped. Color (upperside): Between violet group 88 A and violet-blue group 89 A. Under cooler temperatures and more intensive lighting, the purplish blue tends to intensify. Color (underside): Violet group 88 A to B. Borne: Each flower stem carries 11–13 and more flowers on strong, upright peduncles that are free standing above the leaves, thereby forming a bouquet. Flowering habit: Flowers 10–11 weeks after planting an unrooted plantlet.

*Reproductive organs.*—Stamens: Five (5). Anthers: 5 composed of 10 anther cells, seed capsule pushes slightly through. Filaments: Yellowish green with purplish blue at base, 4–5 mm long.

Styles: 8–9 mm long, purplish blue, base of ovary light green and hairy.

*Roots.*—Normally developed, white when young, turning slightly brownish when older.

*Disease resistance.*—Up to date, Mexico City has shown very good resistance to all major violet diseases.

General observations

Mexico City is an attractive cultivar due to its extra large growth habit. It is designed to be grown in a 15 cm pot (instead of the regular 10 cm pot) and will grow as large as 35–45 cm in diameter. (The diameter can vary depending on how firmly the potting medium is compressed). A nice bouquet of flowers free standing above the leaves develops 10–11 weeks after planting an unrooted plantlet. Each of the 10–12 and more strong flower stems carries 11–13 and more large star-shaped, dark purplish blue flowers with wavy petal tips contrasting nicely with the bright yellow anthers. The flowers are long-lasting and non-dropping. The bouquet is surrounded by very large, dark green, heart-shaped, slightly serrated leaves.

I claim:

1. A new and distinct cultivar of African violet plant named Mexico City, as described and illustrated, and particularly characterized by its extra large growth habit (35–45 cm in diameter); large, star-shaped, dark purplish blue flowers with wavy petal tips; strong stems which curve toward the center to form a bouquet above the leaves; profuse flowering; very large, dark green, heart-shaped leaves; flowering 10–11 weeks after planting of unrooted shoot, and by its long lasting and non-dropping flowers.

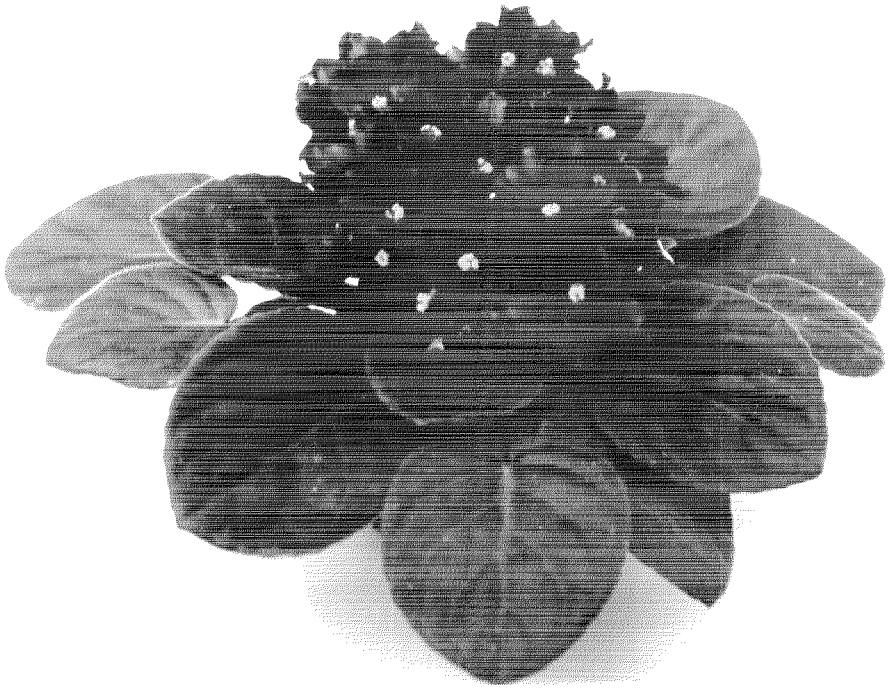

* * * * *